(12) United States Patent
Weda et al.

(10) Patent No.: US 10,321,851 B2
(45) Date of Patent: Jun. 18, 2019

(54) METHOD OF DETECTING ARDS AND SYSTEMS FOR DETECTING ARDS

(71) Applicant: KONINKLIJKE PHILIPS N.V., Eindhoven (NL)

(72) Inventors: Johannes Weda, Nijmegen (NL); Teunis Johannes Vink, Valkenswaard (NL); Yuanyue Wang, Eindhoven (NL); Lieuwe Durk Jacobus Bos, Amsterdam (NL); Tamara Mathea Elisabeth Nujsen, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 207 days.

(21) Appl. No.: 15/117,469

(22) PCT Filed: Feb. 11, 2015

(86) PCT No.: PCT/EP2015/052806
§ 371 (c)(1),
(2) Date: Aug. 9, 2016

(87) PCT Pub. No.: WO2015/124468
PCT Pub. Date: Aug. 27, 2015

(65) Prior Publication Data
US 2016/0345859 A1 Dec. 1, 2016

(30) Foreign Application Priority Data
Feb. 19, 2014 (EP) .................................. 14155767

(51) Int. Cl.
*A61B 5/08* (2006.01)
*A61M 16/10* (2006.01)
(Continued)

(52) U.S. Cl.
CPC .............. *A61B 5/082* (2013.01); *A61B 5/097* (2013.01); *A61B 5/7275* (2013.01);
(Continued)

(58) Field of Classification Search
None
See application file for complete search history.

(56) References Cited

U.S. PATENT DOCUMENTS

| 6,540,691 B1 | 4/2003 | Phillips |
| 2002/0155166 A1 | 10/2002 | Choi et al. |

(Continued)

FOREIGN PATENT DOCUMENTS

| CN | 102300502 A | 12/2011 |
| WO | 0041623 A1 | 7/2000 |

(Continued)

OTHER PUBLICATIONS

Silva, Lurdes IB, et al. "Breath analysis by optical fiber sensor for the determination of exhaled organic compounds with a view to diagnostics." Talanta 83.5 (2011): 1586-1594.*

(Continued)

*Primary Examiner* — Patricia Mallari
*Assistant Examiner* — Jairo H Portillo

(57) ABSTRACT

The invention is directed to a system and method for providing an ARDS indication of a patient comprising a sampling device for obtaining a gas sample of the exhaled breath of a patient, a measuring unit for measuring a content of n-octane in the exhaled breath of a patient, a controller which is able to distinguish if the patient has or may develop ARDS based on the content of n-octane in the exhaled breath of a patient resulting in a ARDS indication of the patient and provided with a protocol for providing output regarding the ARDS indication of the patient, and a user interface for indicating the ARDS indication to a user.

20 Claims, 2 Drawing Sheets

(51) Int. Cl.
| | |
|---|---|
| A61M 16/08 | (2006.01) |
| A61B 5/097 | (2006.01) |
| A61B 5/00 | (2006.01) |
| A61M 16/04 | (2006.01) |
| A61M 16/06 | (2006.01) |
| G01N 33/497 | (2006.01) |
| A61M 16/00 | (2006.01) |

(52) U.S. Cl.
CPC .............. *A61B 5/7282* (2013.01); *A61B 5/74* (2013.01); *A61M 16/024* (2017.08); *A61M 16/04* (2013.01); *A61M 16/06* (2013.01); *A61M 16/085* (2014.02); *A61M 16/0875* (2013.01); *A61M 16/1045* (2013.01); *G01N 33/497* (2013.01); *A61B 2505/03* (2013.01); *A61M 2016/0033* (2013.01); *A61M 2230/437* (2013.01); *G01N 2033/4975* (2013.01)

(56) References Cited

U.S. PATENT DOCUMENTS

| | | | |
|---|---|---|---|
| 2009/0042309 A1* | 2/2009 | Van Herpen | A61B 5/097 436/133 |
| 2009/0054798 A1 | 2/2009 | Varney et al. | |
| 2010/0137733 A1* | 6/2010 | Wang | A61B 5/08 600/532 |
| 2011/0046497 A1 | 2/2011 | Abraham-Fuchs et al. | |
| 2011/0118569 A1* | 5/2011 | Shi | G01N 33/92 600/309 |
| 2011/0269632 A1* | 11/2011 | Haick | B82Y 15/00 506/7 |
| 2013/0029937 A1* | 1/2013 | Amrein | A61K 45/06 514/58 |
| 2013/0143247 A1 | 6/2013 | Haick et al. | |

FOREIGN PATENT DOCUMENTS

| | | |
|---|---|---|
| WO | 2009098627 A1 | 8/2009 |
| WO | 2010065452 A1 | 6/2010 |
| WO | 2013118098 A1 | 8/2013 |
| WO | 2013121374 A2 | 8/2013 |

OTHER PUBLICATIONS

Barnett et al: "Biomarkers in Acute Lung Injury-Marking Forward Progress"; Crit Care Clin. Jul. 2011, vol. 27 (3), pp. 661-683.
Bajtarevic et al: "Noninvasive Detection of Lung Cancer by Analysis of Exhaled Breath"; BMC Cancer 2009, vol. 9, pp. 1-16.
Boots et al: "The Versatile Use of Exhaled Volatile Organic Compounds in Human Health and Disease"; J. Breath Res. 6 (2012), pp. 1-21.
Bos et al: "Metabolomics in Critically Ill Patients: Folcus on Exhaled Air"; Annual Update in Intensive Care and Emergency Medicine, 2012, pp. 53-62.
Bos et al: "A Simple Breath Sampling Method in Intubated and Mechanically Ventilated Critically Ill Patients"; Respiratory Physiology & Neurobiology, vol. 191, Jan. 2014, pp. 67-74.
Cao et al: "Breath Analysis: Potential for Clinical Diagnosis and Exposure Assessment"; Clinical Chemistry 52.5, (2006) pp. 1-12.
Carpenter et al: "Exhaled Breath Condensate Isoprostanes Are Elevated in Patients With Acute Lung Injury or ARDS"; Chest, vol. 114, Dec. 1998, pp. 1653-1659.
Chastre et al: "Ventilator-Associated Pneumonia"; Am J Respir Crit Care Med, vol. 165, pp. 867-903, 2002.
Crader et al: "Breath Biomarkers and the Acute Respiratory Distress Syndrome"; J. Pulmonary Repiration Med, 2012, vol. 2, Issue 1, pp. 1-9.

Fens et al: "Exhaled Breath Profiling Enables Discrimination of Chronic Obstructive Ulmonary Disease and Asthma"; Am J. Respir Care Med., vol. 180, pp. 1076-1082, 2009.
Friedrich: "Scientists Seek to Sniff Out Diseases: Electronic "Noses" May Someday Be Diagnostic Tools"; JAMA, Feb. 2009, vol. 301, No. 6, pp. 585-586.
Gajic et al: Early Identication of Patients at Risk of Acute Lung Injury; Am J Respir Crit Care Med, vol. 183, pp. 462-470, 2011.
Haick et al: "Sniffing Chronic Renal Failure in Rat Model by an Array of Random Networks of Single-Walled Carbon Nanotubes"; American Chemical Society, vol. 3, No. 5, 2009, pp. 1258-1266.
Hubschmann:Handbook of GC/MS: Fundamentals and Applications, Second Edition (Berlin: Wiley), 2009 Book—732 Pages.
Millo et al: "Compartmentalisation of Cytokines and Cytokine Inhibitors in Ventilator-Associated Pneumonia"; Intensive Care Med (2004), vol. 30, pp. 68-74.
Moser et al: "Mass Spectrometric Profile of Exhaled Breath-Field Study by PTR-MS"; Respiratory Physiology & Neurobiology, vol. 145 (2005), pp. 295-300.
"Ventilation With Lower Tidal Volume as Compared With Traditional Tidal Volumes For Acute Lung Injury and the Acute Respiratory Distress Syndrome"; New England Journal of Medicine, vol. 342, No. 18, May 2000, pp. 1301-1308.
Nelson et al: "Compartmentalization of Intraalveolar and Systemic Lipopolysaccharide-Induced Tumor Necrosis Factor and the Pulmonary Inflammatory Response"; The Journal of Infectious Diseases, vol. 159, No. 2, Feb. 1989, pp. 189-194.
Pauling et al: "Quatitative Analysis of Urine Vapor and Breath by Gas-Liquid Partition"; Proceedings of the National Academy of Sciences of the United States of America, vol. 68, No. 10, Oct. 1971, pp. 2374-2376.
Peng et al: "Detection of Lung, Breast, Colorectal, and Prostate Cancers From Exhaled Breath Using a Single Array of Nanosensors"; British Journal of Cancer (2010), vol. 103, pp. 542-551.
Phillips et al: "Volatile Organic Compounds in Breath As Markers of Lung Cancer: A Cross-Sectional Study"; Lancet 1999, vol. 353, pp. 1930-1933.
Poli et al: "Exhaled Volatile Organic Compounds in Patients With Non-Small Cell Lung Cancer:Cross Sectional and Nested Short-Term Follow-Up Study"; Respiratory Research, Jul. 2005, vol. 6, pp. 1-10.
Pugin et al: "The Alveolar Space Is the Site of Intense Inflammatory and Profibrotic Reactions in the Early Phase of Acute Respiratory Distress Syndrome"; Crit Care Med 1999, vol. 27, No. 2, pp. 301-312.
Schultz et al: "Local Activation of Coagulation and Inhibition of Fibrinolysis in the Lung During Ventilator Associated Pneumonia"; Thorax 2004, vol. 59, p. 130-135.
Slutsky: "Lung Injury Caused by Mechanical Ventilation"; Chest, 1999, vol. 116, SUPP_1, pp. 9S-15S.
Tisato: "Detection of Volatile Organic Compounds in the Alveolar Air of Subjects With Stress-Related Psychopathologies"; Thesis, University of Verona, 50 Page Document, 2010.
Tzouvelekis et al: Serum Biomarkers in Acute Respiratory Distress Syndrome an Ailing Prognosticator, Respiratory Research 2005, 6:62, pp. 1-19.
Van De Kant: "Non-Invasive Measaurements in Wheezing Preschool Children"; Jun. 2011, Thesis, Maastricht University, 192 Page Document.
Van De Kant et al: "Clinical Use of Exhaled Volatile Organic Compounds in Pulmonary Diseases: A Systematic Review"; Respiratory Research, 2012, 13:117, pp. 1-23.
Dallinga et al: "Volatile Organic Compounds in Exhaled Breath as a Diagnostic Tool for Asthma in Children"; Clinical Experimantal Allergy, 40, 2009, pp. 68-76.
Mashir et al: "Exhaled Breath Analysis: The New Interface Between Medicine and Engineering": Advanced Powder Technology 20 (2009) pp. 420-425.

* cited by examiner

METHOD OF DETECTING ARDS AND SYSTEMS FOR DETECTING ARDS

CROSS-REFERENCE TO PRIOR APPLICATIONS

This application is the U.S. National Phase application under 35 U.S.C. § 371 of International Application No. PCT/EP2015/052806, filed on Feb. 11, 2015, which claims the benefit of European Patent Application No. 14155767.8, filed on Feb. 19, 2014. These applications are hereby incorporated by reference herein.

The present invention is directed to a method to determine if a patient has or is developing ARDS. The invention is also directed to a system for detecting acute respiratory distress syndrome, also referred to as ARDS.

The lungs of intubated and mechanically ventilated patients are prone to infection and injury, at least in part because of the artificial airway, use of non-physiologic positive airway pressures and tidal volume/pressure-associated over distension of lung tissue. Prevalent complications include ventilator-acquired pneumonia (VAP) and ventilator-associated lung injury (VALI). Preexistent pulmonary damage, due to pneumonia and/or acute respiratory distress syndrome (ARDS) can be aggravated by mechanical ventilation resulting in increased mortality and morbidity. The clinical manifestation of infection and/or injury, including pulmonary infiltrations on chest X-ray, is preceded by molecular and cellular changes within the lung. Adequate and timely detections of the primary pathophysiological molecular and cellular mechanisms potentially could lead to prompt treatment initiation and targeted therapeutic interventions. Therefore, early and accurate biological markers of pulmonary injury and especially for ARDS are very much needed to either predict ARDS development in a patient or when ARDS has developed to enhance early diagnosis.

A valid and reliable definition for ARDS is furthermore considered important for clinical management and to facilitate enrolment of consistent patient phenotypes into clinical trials. The presently used Berlin criteria are empirically selected clinical, radiological and physiological variables. This definition is highly suitable for epidemiological studies but show a moderate correlation with post-mortem pathological findings. ARDS can still be mistaken for pneumonia or cardiogenic pulmonary edema (CPE), and vice versa.

In Crader et al., J Pulmonar Respirat Med 2012, 2:1 a number of potential biomarkers are described to predict ARDS for a patient. This overview paper states that a number of approaches for assessing biomarkers in breath and breath condensates have been proposed but none used so far. The paper also mentions that the potential for using breath biomarkers is substantial because it could provide a non-invasive way of directly and repeatedly analyzing the conditions which may contribute to ARDS development.

Currently chest X-rays allow diagnosis of ARDS in advanced stages. A disadvantage is that it exposes patients to radiation doses. Airway suction or lavage provides early detection. A disadvantage of these methods is that they are invasive and harmful to the patient. All of the above methods are furthermore not suitable for frequent checks if a patient has or may develop ARDS.

The invention is directed to method and systems which could provide adequate and timely detections of ARDS which could lead to prompt treatment initiation and targeted therapeutic interventions.

This is achieved by the following method. A method comprising sampling part of the exhaled breath of a patient to obtain a gas sample, measuring the content of n-octane in the gas sample and determining if the patient has ARDS or may develop ARDS using the measured content of n-octane in the gas sample.

Applicants found that higher contents of n-octane in exhaled breath is indicative for ARDS compared to the content of n-octane in the exhaled breath of patients not having ARDS. Thus n-octane is a suited breath biomarker for assessing if a patient has developed ARDS. This method thus enhances timely detection of ARDS. The method is further found to be not influenced by severity of the ARDS illness, ventilator settings or comorbidities.

The invention is also directed to a system for providing an ARDS indication of a patient comprising a sampling device for obtaining a gas sample of the exhaled breath of a patient, a measuring unit for measuring a content of n-octane in the exhaled breath of a patient, a controller which is able to distinguish if the patient has or may develop ARDS based on the content of n-octane in the exhaled breath of a patient resulting in a ARDS indication of the patient and provided with a protocol for providing output regarding the ARDS indication of the patient, and a user interface for indicating the ARDS indication to a user.

Preferably, the method is used for mechanically ventilated patients, invasively, for example via intubation, or non-invasively, for example using a mask. The method may be performed at home, in service flats, nursing homes and in hospitals. The method is especially suited for patients treated in an intensive care unit of a hospital.

The determining if the patient may develop ARDS and more especially if the patient has ARDS by using the measured content of n-octane in the gas sample may be performed by determining if the measured content is above a predetermined threshold value which has been found to be predictive for ARDS. It may also be envisaged that the sensitivity of the prediction for some values of the n-octane content is not sufficient for practical use and that additional validation is required. Possible additional measurements and data for such validation will be discussed below. When the n-octane content is measured continuously or semi-continuously, for example when performing the method on-line, it may also be possible to use the rate of increase in n-octane content in the patients exhaled breath as the measurement determining if the patient has ARDS or may develop ARDS. The determination if a patient has ARDS or may develop ARDS may be communicated to a user by means of a user interface as will be further described below.

Applicants further found that lower acetaldehyde and/or 3-methylheptane contents are also indicative for ARDS when compared to the content of acetaldehyde and/or 3-methylheptane in exhaled breath of patients not having ARDS. Preferably the measured content of either one or both of these compounds is used to determine if the patient has ARDS or may develop ARDS. More preferably the measured content of either one or both of these compounds is used to validate the relevancy of the measured content of n-octane when determining if the patient has ARDS or may develop ARDS. Applicants found that when a content of n-octane is measured which lies in a region which is less significant for determining ARDS such additional data will improve the sensitivity of the method. In addition or alternatively the sensitivity of the method may also be improved using other patient parameters. With other patient parameters is meant any information regarding the patient not being the above described content of n-octane, acetaldehyde and/or 3-methylheptane in the exhaled breath of the patient. Such other patient parameters may be for example the ventilator settings and/or parameters, the patient monitoring data, such as for example heart rate, oxygenation, body temperature, and patient history data, such as for example pneumonia, heart failure, sepsis, and pancreatitis. An example of such other patient parameters comprises the lung injury prediction score (LIPS) of the patient. Applicants found that the LIPS can be used to validate the relevancy of the measured content of n-octane when determining if the patient has ARDS or may develop ARDS. The lung injury prediction score (LIPS) is well known and described by Gaijc O., et al in Am J Respir Crit Care Med 2011 Feb 15; 183(4):462-70.

The method comprises sampling part of the exhaled breath of a patient to obtain a gas sample and subsequent measurement of the gas sample as to its n-octane and optionally also to its acetaldehyde and/or 3-methylheptane content. Breath may be sampled and measured off-line or online The sampling device of a system for use in such an off-line method suitably comprises a sorbent tube and/or an air bag. An example of an off-line performed method is the following, wherein a patient breathes into an air bag, for example a Tedlar bag, for a certain amount of time. This results in that the bag is filled with the exhaled breath of the patient. The contents of the air bag may be measured directly. Alternatively a pump and a mass flow controller may be connected to the bag and the collected air is pushed or pulled with a fixed flow for a fixed amount of time through a sorbent tube. Mechanically ventilated patients, which are unable to breathe in a bag, may be sampled off-line by means of a small pump at the bed side which pulls breath samples directly through a sorbent tube. The thus obtained sorbent tube will contain a representative amount of the compounds present in the exhaled breath of the patient.

Subsequently the content of n-octane and optionally acetaldehyde and/or 3-methylheptane as present in the sampling device may be measured by means of analytical techniques. Preferably such a technique is a spectroscopy technique for example Time Of Flight Mass Spectrometry (TOF-MS), infra-red spectroscopy and Ion Mobility Spectrometry (IMS) and preferably Gas Chromatography Mass-Spectrometry (GC-MS). These techniques provide knowledge on individual molecular compounds and can provide precise measures on the n-octane content and the optional acetaldehyde and/or 3-methylheptane content in a breath sample. Sampling part of the exhaled breath may thus be performed using a sorbent tube and measuring the content is performed by means of gas-chromatography and mass-spectrometry (GC-MS). Such a method however requires rather laborious procedures, relatively large devices and trained operators.

For the above reason the method is preferably performed on-line. In such an on-line method the breath of a patient is passively or actively transported to a sensor or array of sensors. For monitoring this approach has a preference due to the ease and speed of processing. Using this method the breath analyzer can be embedded in the device that samples breath from the ventilator hoses, for example by using a pump. The on-line measurement of the content of n-octane and the optional acetaldehyde and/or 3-methylheptane in the breath samples may be performed by for example so-called Electronic Noses (eNoses) or miniaturized spectroscopy units as for example miniaturized GC (microGC) and/or Mass Spectrometry, Ion Mobility Spectroscopy (IMS)) and/or FAIMS (High-Field Waveform IMS). Preferably such a breath analyzer is adapted to measure n-octane and optionally acetaldehyde and/or 3-methylheptane specifically.

An eNose consists of an array of non-specific gas chemical sensors combined with a chemometric processing tool. Different techniques exist for the precise type of chemical sensor and chemometric processing method. The choice of sensor and processing method will be based upon n-octane and optionally also acetaldehyde and/or 3-methylheptane. A possible measuring method may be based on molecular imprinting or optical techniques using infrared lighting. A skilled person will know that by adjusting the threshold while balancing sensitivity and specificity, an optimal setting can be found for such a device.

A more preferred on-line method is wherein a breath analyzer is embedded in the ventilator system or embedded in the patient monitor. This prevents the need for an additional device at the patient's bedside, and allows continuous monitoring of breath. Additionally, the lungs of ARDS patients are vulnerable to changes in pressure. Coupling or decoupling an additional device to the ventilator tubes may negatively influence the continuous pressure in the mechanical ventilator system, and may therefore damage the lungs. For embedding the breath analysis into the ventilator system eNose type of techniques can be used, or a dedicated n-octane, acetaldehyde and/or 3-methylheptane sensor as for example the miniaturized spectroscopy units described above.

The invention is also directed to n-octane for use in in-vivo diagnosis of ARDS and to acetaldehyde and/or 3-methylheptane for use in in-vivo diagnosis of ARDS.

The invention is also directed to a system described above. Such a system for providing an ARDS indication of a patient comprises a sampling device for obtaining a gas sample of the exhaled breath of a patient. The system further comprises a measuring unit for measuring a content of n-octane and optionally acetaldehyde and/or 3-methylheptane in the exhaled breath of a patient. The system also comprises a controller which is able to distinguish if the patient has or may develop ARDS based on the content of n-octane, acetaldehyde and/or 3-methylheptane in the exhaled breath of a patient resulting in a ARDS indication of the patient and provided with a protocol for providing output regarding the ARDS indication of the patient. The controller may suitably use the logic for determination if a patient has ARDS or may develop ARDS as described above for the method according to the invention. The system also comprises a user interface for indicating the ARDS indication to a user. Such a user interface may be present at the point of care, may be part of the monitor of a mechanical ventilator unit or may even be mobile interface which can be used in combination with more than one system according to the invention.

Preferably the measuring unit is a unit for measuring a content of n-octane and the controller is preferably able to distinguish if the patient has or may develop ARDS based on the content of n-octane in the exhaled breath of a patient and more especially according to the method described above.

The sampling device may be suited for off-line measurement of the content of the specific compounds in the exhaled breath. Suitably the sampling device comprises a sorbent tube and or an air bag and the measuring unit is a spectroscopy measuring unit as described for the above method.

More preferably the sampling device and measuring unit enable an on-line measurement of the exhaled breath. As explained above such a sampling device suitably is a device which samples breath from a ventilator hose which is part of a system to mechanically ventilate a patient. The measuring unit of such an on-line system is suitably the afore mentioned Electronic Nose, miniaturized spectroscopy units as for example miniaturized forms of GC (microGC) and/or Mass Spectrometry, Ion Mobility Spectroscopy (IMS) and/or FAIMS (High-Field Waveform IMS), wherein such measuring unit is specifically adapted to measure n-octane and optionally acetaldehyde and/or 3-methylheptane.

BRIEF DESCRIPTION OF THE DRAWINGS

Preferably the method and system should not interfere with the ventilator in terms of pressures and flows, especially in the context of regulatory issues. Therefore, a side stream approach is preferred as for example illustrated in FIG. 1. FIG. 1 shows a schematic set up for an off-line system wherein air from a mechanically ventilated patient 4 is sampled using a so-called side stream approach. The exterior part of an intubation tube 5 is shown which is connected to a ventilator unit 7 via conduit 6 and a heat and humidity exchanger (HME) 3. Ventilator unit 7 may comprise of a flow sensor, a controller and a gas flow generator. The air is collected via side stream conduit 8 using pump and flow controller 1. Pump and flow controller 1 enable a controlled flow of exhaled breath to pass sorbent tube 2 using a small mechanical pump. An on-line system may be as in FIG. 1 wherein a sorbent tube is not incorporated. In such a system the pump and flow controller 1 also comprises of a measurement unit for measuring the content of n-octane and optionally acetaldehyde and/or 3-methylheptane. Suitably such a side stream approach is integrated in the ventilator device, avoiding extra devices at the bedside, and avoiding abrupt pressure changes in the ventilator systems, which may harm the vulnerable lungs.

EXAMPLES

Figure 1:
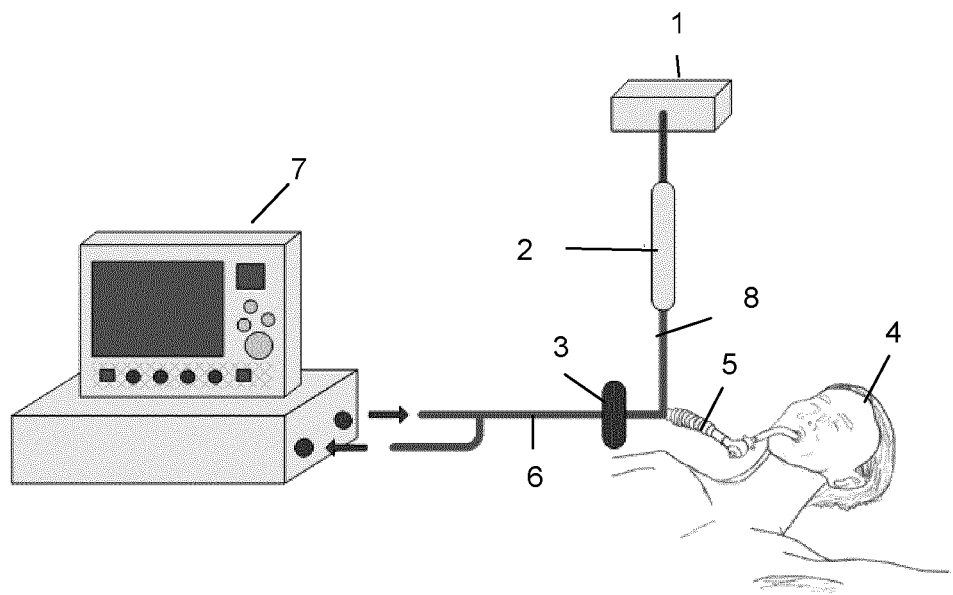
FIG. 1 diagrammatically shows a system used for mechanically ventilating a patient according to one aspect.
Figure 2:
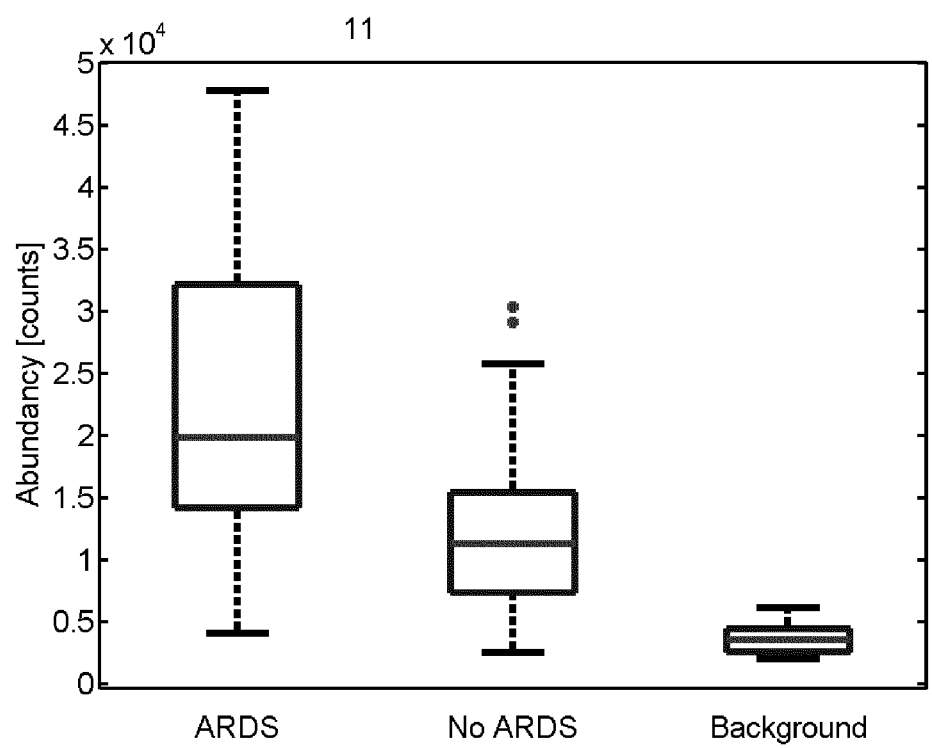
FIGS. 2 and 3 shows a graphs of data collected from the system of FIG. 1.
Figure 3:
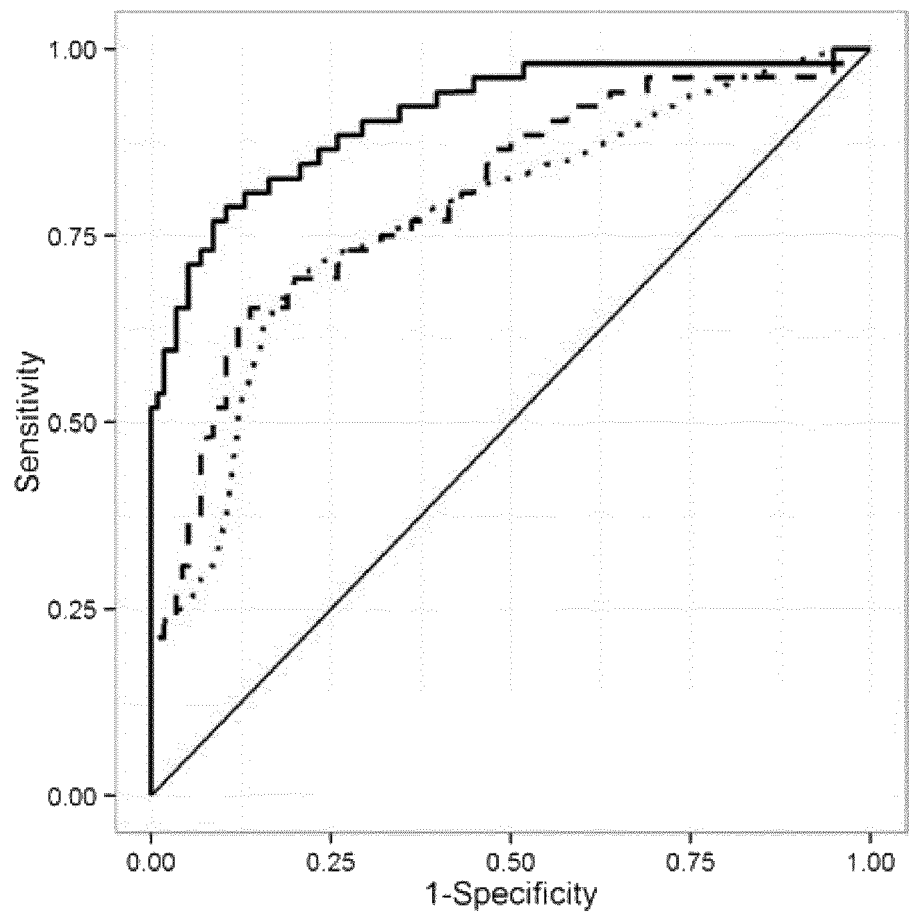

In a clinical trial with 54 mechanically ventilated intensive care unit patients (24 ARDS, 30 non-ARDS) have been subjected to an exhaled breath analysis using a system as in FIG. 1. The content of n-octane in the sorbent tubes were analyzed by means of gas-chromatography and mass-spectrometry (GC-MS). In FIG. 2 the results are presented. In this Figure a significant difference in abundance of n-octane for patients having ARDS is observed in comparison with the abundance of n-octane in the exhaled breath of patients not having ARDS. The abundancy of n-octane is expressed in counts of the GC-MS fragment at m/z=114, as measured by the mass-spectrometer as part of the GC-MS which uses electron ionization to produce fragments of different mass over charge (m/z). Building a classifier model, and internally validating this, has shown that by using breath analysis and monitoring n-octane abundance we can distinguish patients with ARDS from patients without ARDS. This is illustrated by FIG. 3. FIG. 3 shows a so-called receiver operating characteristic (ROC) curve. FIG. 3 shows three curves:

A dashed line which represents the performance of a classifier based on n-octane (C8) on distinguishing ARDS patients (AUC: 0.80 (95%-CI: 0.71-0.88).

A dotted line represents the performance of a classifier based on LIPS on distinguishing ARDS patients (AUC: 0.78 (95%-CI: 0.70-0.87).

A solid line represents the performance of a classifier based on n-octane (C8) and validated by LIPS on distinguishing ARDS patients (AUC: 0.91 (95%-CI: 0.85-0.97).

The results in FIG. 3 show that n-octane is a good biomarker for ARDS and that the sensitivity at a given specificity can be even further enhanced by validating the measured n-octane content with the LIPS of the patient.

In their experiments applicants further identified acetaldehyde and 3-methylheptane as suitable biomarker for ARDS. They further found no differences in exhaled isoprene concentrations between patients with and without ARDS were observed. Isoprene was reported as a biomarker by Schubert et al. Application of a new method for analysis of exhaled gas in critically ill patients. Intensive Care Med 1998;24:415-421. The difference in results is believed to result from the fact that the patients in this study were included within 24 hours after ICU-admission, thereby early in the development of ARDS, whereas the patients in the study of Schubert et al. were included later during the course of disease. Thus the method and system according to the present invention is more effective in detecting the early development of ARDS.

The invention claimed is:

1. A system for providing an Acute Respiratory Distress Syndrome (ARDS) indication of a patient comprising:
   a sampling device for obtaining a gas sample of the exhaled breath of a patient,
   a measuring unit for measuring a content of n-octane in the gas sample of the exhaled breath of the patient,
   a controller comprising a mechanical ventilator system programmed to determine an ARDS indication that the patient has or may develop ARDS based on the content of n-octane in the gas sample of the exhaled breath of the patient exceeding a predetermined threshold value, and
   a user interface comprising a monitor of the mechanical ventilator system for indicating the ARDS indication that the patient has or may develop ARDS to a user.

2. The system according to claim 1, wherein:
   the measuring unit further measures a content of acetaldehyde and/or 3-methylheptane; and
   the controller determines the ARDS indication further based on the content of acetaldehyde and/or 3-methylheptane in the gas sample of the exhaled breath of a patient.

3. The system according to claim 1, wherein the sampling device comprises a sorbent tube and/or an air bag.

4. The system according to claim 3, wherein the measuring unit comprises a Time Of Flight Mass Spectrometry (TOF-MS), Ion Mobility Spectrometry (IMS), or Gas Chromatography Mass-Spectrometry (GC-MS) device.

5. The system according to claim 1, wherein:
   the sampling device is a side stream sampling device including a pump and flow controller connected via a side stream conduit to sample exhaled air from a ventilator hose via which the patient is mechanically ventilated by the mechanical ventilator system; and
   the measuring device comprises a Gas Chromatography Mass Spectrometry (GC-MS), Ion Mobility Spectroscopy (IMS), and/or High-Field Waveform IMS device.

6. The system according to claim 5, wherein:
   the side stream sampling device and the measuring device operate to measure the content of n-octane in the gas sample of the exhaled breath of the patient continuously; and the controller determines the ARDS indication further based on a rate of increase in n-octane content in the gas sample of the exhaled breath of the patient.

7. The system according to claim 1, wherein the controller determines the ARDS indication further based on other patient parameters.

8. The system according to claim 7, wherein the other patient parameters comprises the lung injury prediction score (LIPS) of the patient.

9. A method comprising the steps of:
providing a system for providing an Acute Respiratory Distress Syndrome (ARDS) indication of a patient comprising a sampling device for obtaining a gas sample of the exhaled breath of a patient, a measuring unit for measuring a content of n-octane in the exhaled breath of a patient, a controller comprising a mechanical ventilator system which is able to distinguish if the patient has or may develop ARDS based on the content of n-octane in the exhaled breath of a patient resulting in an ARDS indication of the patient and provided with a protocol for providing output regarding the ARDS indication of the patient, and a user interface comprising a monitor of the mechanical ventilator system for indicating the ARDS indication to a user; sampling part of the exhaled breath of the patient to obtain the gas sample,
measuring the content of n-octane in the gas sample determining if the content of n-octane in the gas sample is above a predetermined threshold value; and
indicating, on the user interface, the ARDS indication to the user based on the determining step.

10. A method according to claim 9, wherein the threshold value has been determined to be predictive for Acute Respiratory Distress Syndrome (ARDS).

11. Method according to claim 9, wherein the threshold value has been determined by balancing sensitivity and specificity of a chemical sensor used for the sampling to obtain the gas sample and the measuring the content of n-octane in the gas sample.

12. Method according to claim 9, wherein the content of acetaldehyde and/or 3-methylheptane is measured and wherein determining if the patient has ARDS or may develop ARDS is performed by using the measured content of n-octane and the measured content of acetaldehyde and/or 3-methylheptane in the gas sample.

13. Method according to claim 9, wherein sampling part of the exhaled breath is performed using a sorbent tube and/or an air bag.

14. Method according to claim 9, wherein the sampling and measurement of the content is performed on-line.

15. Method according to claim 9, wherein the patient is a mechanically ventilated patient.

16. Method according to claim 9, wherein other patient parameters are used to validate the relevancy of the measured content of n-octane when determining if the patient has ARDS or may develop ARDS.

17. Method according to claim 16, wherein the other patient parameters comprises the lung injury prediction score (LIPS) of the patient.

18. A method comprising the steps of:
obtaining a gas sample of exhaled breath of a patient,
measuring a content of n-octane in the gas sample of exhaled breath of a patient using Time Of Flight Mass Spectrometry (TOF-MS), Ion Mobility Spectrometry (IMS), Gas Chromatography Mass-Spectrometry (GC-MS), and/or High-Field Waveform IMS,
using a controller of a mechanical ventilator system, determining if the patient has Acute Respiratory Distress Syndrome (ARDS) or may develop ARDS by determining if the measured content of n-octane in the gas sample is above a predetermined threshold value; and
presenting an ARDS indication to the user on a monitor of the mechanical ventilator system if it is determined in the determining step that the patient has ARDS or may develop ARDS.

19. The method according to claim 18, wherein one of:
(i) the obtaining of the gas sample of exhaled breath of the patient comprises obtaining the gas sample using a sorbent tube and/or an air bag, or
(ii) the obtaining of the gas sample of exhaled breath of the patient comprises obtaining the gas sample using side stream sampling to obtain the gas sample via a side stream conduit from a ventilator hose via which the patient is mechanically ventilated by the mechanical ventilator system.

20. The method according to claim 18, wherein:
the measuring further includes measuring a content of acetaldehyde and/or 3-methylheptane in the gas sample of exhaled breath of the patient; and
the determining is further based on the content of acetaldehyde and/or 3-methylheptane in the gas sample of exhaled breath of the patient.

* * * * *